United States Patent [19]

Moskowitz

[11] 4,073,321

[45] Feb. 14, 1978

[54] ADJUSTABLE BLOCKING MEANS FOR DOSAGE REGULATION

[76] Inventor: George Moskowitz, 101 B. Rutledge Ave., Charleston, S.C. 29401

[21] Appl. No.: 666,957

[22] Filed: Mar. 15, 1976

[51] Int. Cl.² .............................................. B65B 3/04
[52] U.S. Cl. ............................ 141/27; 128/218 C
[58] Field of Search ............... 141/2, 1, 18, 21, 27, 141/94, 115, 116, 367, 368, 369, 370, 371, 372, 373, 378; 222/309; 128/218 C; 23/253, 259; 73/425.6; 33/1 V

[56] References Cited

U.S. PATENT DOCUMENTS

| 3,492,876 | 2/1970 | Bull et al. ............................ 141/27 |
| 3,770,026 | 11/1973 | Isenberg ............................ 141/27 |
| 3,965,945 | 6/1976 | Ross ................................... 141/27 |

Primary Examiner—Houston S. Bell
Attorney, Agent, or Firm—Larry Harold Kline

[57] ABSTRACT

A device is disclosed for regulating the dosage of a fluid in a syringe by using blocking means to control the amount of fluid which may be taken into the barrel of the syringe.

18 Claims, 3 Drawing Figures

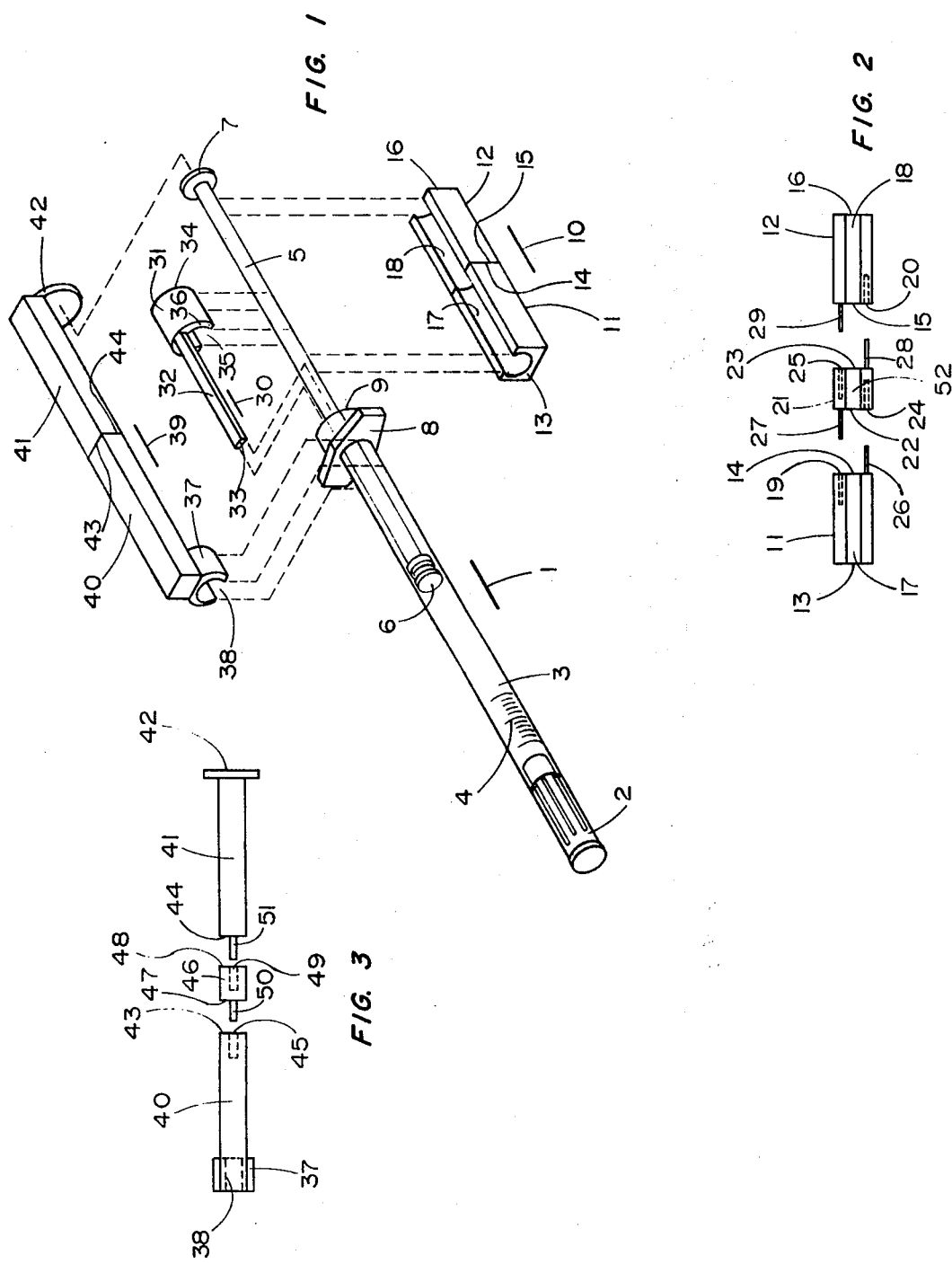

ADJUSTABLE BLOCKING MEANS FOR DOSAGE REGULATION

This invention relates to a device which aids in obtaining exact dosages of medicine within syringes and, more particularly to a device which may be used to obtain exact dosages without dependency on eyesight. Many persons find it necessary to give themselves injections of insulin or other medications. A basic problem exists in loading the syringe with the proper dosage of medication.

Persons who have sight impediments and many unskilled or unintelligent parents or patients face the constant problem of concern over the proper amount of medication. The present invention solves this problem in three ways by using blocking means in conjunction with the syringe.

There have been other devices designed and patented such as the Adjustable Syringe Dose Aid of Floyd Andrew Wright, U.S. Pat. No. 3,840,011, and others. The Inventor believes the present invention to be much simpler and less expensive than the previous inventions.

An object of the present invention is to provide a device from which the proper dosage of medication in a syringe may be obtained by a blind or unskilled person.

Another object of this invention is to provide a device that is adjustable for obtaining varying dosages of medication in a syringe without dependency on eyesight.

Still another object of this invention is to provide a device for obtaining accurate dosages of medication which is reusable and relatively inexpensive.

These and other objects and features of the invention will be apparent from the following description and appended claims.

Briefly, the invention is a device for regulating the dosage of a fluid in a syringe. Blocking means may be placed between the plunger end of the syringe and the stop at the top of the syringe fluid-holding barrel. When the plunger end is pressed toward the top, the blocking means allows excess fluid to be rejected from the barrel and retains only the desired dosage of the fluid in the barrel. The blocking means comprises a plurality of sections secured together and a plurality of trough-type openings. There is one trough-type opening in each of the plurality of sections. The plurality of trough-type openings form a single opening of a length equal to the total length of the plurality of trough-type openings. The plunger of the syringe may be placed within the single trough-type opening with sufficient pressure to secure the regulator to the plunger. The plurality of sections may comprise two end sections and a plurality of center sections. The plurality of center sections may be added to increase the length of the regulator and thereby change the desired dosage of the fluid in the barrel. Each of the two end sections may have a blocking end which may press against either the plunger end of the syringe, or the stop at the top of the syringe fluid-holding barrel, and a connecting end which is secured to another of the plurality of sections of the regulator. Each of the two end sections may further comprise an insert extending from the connecting end and an opening in the connecting end. The two end sections may be secured together by placing the insert on the first end section into the opening on the second end section, and the insert on the second end section into the opening in the first end section. Each of the plurality of center sections has two connecting ends fo securing the plurality of center sections to the two end sections. Each of the two connecting ends has an insert extending from it and an opening extending into it. Blocking means may also be placed within the syringe fluid-holding barrel, pressing against the syringe plunger head. The syringe plunger head is thereby restricted from movement past a pre-determined point, restricting the quantity of fluid which may be drawn into the fluid-holding barrel to a pre-determined dosage. The blocking means may also be pressed against the stop at the top of the syringe fluid-holding barrel. The blocking means may be a regulator comprising a plunger grip and a shaft. The plunger grip may have two ends and an opening, and is operative to attach the regulator to the syringe plunger. The shaft is connected to the plunger grip and extends within the syringe barrel, and presses against the syringe plunger head. One end of the plunger grip is pressed against the stop at the top of the syringe barrel, and the second end is pressed against by a force means to stabilize the regulator. The syringe plunger fits snugly within the opening within the plunger grip in order to secure the regulator to the syringe plunger. The shaft may be of varying lengths to change the pre-determined point to which the syringe plunger head may be moved in order to change the pre-determined dosage. Blocking means may also be secured to the syringe barrel and be operative to stop movement of the syringe plunger end. Restricting the movement of the syringe plunger end restricts the quantity of fluid which may be drawn into the syringe barrel to a predetermined dosage. The blocking means may be a regulator comprising a plurality of sections secured together, a barrel grip and a plunger stop. The barrel grip is connected to the end of one of the plurality of sections and secures the regulator to the syringe barrel. The plunger stop is connected to the end of another of a plurality of sections and is operative to restrict movement of the syringe plunger. The plurality of sections comprises two end sections and a plurality of center sections. The plurality of center sections may be added to increase the length of the regulator and thereby change the desired dosage of the fluid in the syringe barrel. One of the two end sections contains a bar grip and a first connecting means. The other of the two end sections contains a plunger stop and a second connecting means. The first and second connecting means are an insert in one end section and an opening in the other end section. The insert may be placed in the opening to secure the end sections together. Each of the plurality of center sections has two ends with an insert extending from one end and an opening in the other end. A desired number of center sections may be secured between the two end sections to increase the length of the regulator and thereby change the desired dosage of the fluid in the syringe barrel. The present invention may be used by itself or may be placed on a mat or holder. The holder may hold the syringe and may hold the bottle from which the fluid is being extracted. Any type of frame may be used in connection with the present invention which would enable the transfer of the fluid from a container to the syringe to be easier for the patient. However, no additional apparatus is necessary for the present invention to be used. When using the present invention, a blind person or a person who has difficulty in reading the graduations on the syringe barrel will have no difficulty in obtaining the exact dosage to be used. No sterilization of this invention is necessary. The invention may be used with either reusable or disposable syringes. The invention may be easily detached from the disposable syringes in order to be reused. The amount of dosage may be set by a medical technician or doctor, and the patient should have no fear of receiving the wrong dosage.

The invention will be more fully understood from the following detailed description and appended claims when taken with the drawings in which:

FIG. 1 is an isometric view of a syringe and three syringe dosage regulators.

FIG. 2 is a top view of the regulator 10 shown in FIG. 1.

FIG. 3 is a top view of the regulator 39 shown in FIG. 1.

Referring now to the drawings, FIG. 1 is an isometric view of syringe 1 and three syringe dosage regulators, regulators 10, 30 and 39. Syringe 1 comprises syringe barrel 3, syringe stop 8, barrel opening 9, and plunger 5. Needle cover 2 is shown attached to the syringe barrel 3, covering the needle (not shown), which extends from the syringe barrel 3. Barrel graduated markings 4 are shown on syringe barrel 3. These markings may extend the length of syringe barrel 3 and indicate various dosage levels of medication within syringe barrel 3. Connected to plunger 5 are plunger head 6 and plunger head 7. Under normal operation of the syringe, the plunger 5 extends through barrel opening 9 into syringe barrel 3. The plunger head 6 is of sufficient diameter to press against the inside wall of syringe barrel 3. When the plunger 5 is pressed downward into barrel opening 9, the plunger head 6 presses downward into syringe barrel 3 and presses any liquid or medication within syringe barrel 3 which is between the needle and the plunger head 6 out of the end of the needle. Plunger head 6 seals off the upper portion of syringe barrel 3 from the liquid or medication which may be held in the lower portion of syringe barrel 3.

Regulator section 40 comprises end 43 with opening 45. Regulator section 41 comprises end 44 with insert 51. Regulator section 46 has end 48 with opening 49 and end 47 with attached insert 50. Regulator sections 40, 46 and 41 are secured together by placing insert 51 into opening 49 and insert 50 into opening 45. The inserts are of sufficient diameter to place pressure on the sides of the openings in order to securely fasten the sections together.

FIG. 1 also shows regulator 30. Regulator 30 comprises plunger grip 31 and regulator shaft 32. Plunger 5 is placed within the opening 35 in plunger grip 31. Regulator 30 is secured to plunger 5 by plunger grip 31. Regulator shaft 32 extends through barrel opening and stop 9. When using regulator 30, the end 33 of regulator shaft 32 presses against plunger head 6, thereby determining the distance that plunger head 6 may rise in the syringe barrel 3, and thereby determining the exact dosage of liquid or medication within the syringe barrel 3.

Edge 36 of the plunger grip 31 will press against barrel opening and stop 9. The regulator 30 may be held firmly by applying pressure to end 34 of plunger grip 31. This pressure may simply be applied by the hand of the user, or any other force means.

The regulator 39 could also be adjusted so that the plunger stop 42 was changed to actually fit on the other side of plunger end 7. The plunger end 7 would then by pressed against the opposite side of plunger stop 42 in order to obtain the proper dosage.

The present invention would be of great benefit to those individuals who must administer drugs to themselves or others, and who suffer from poor eyesight or difficulty in understanding the symbols on the syringes.

Regulator 30 may be adjusted to change the dosage by changing the length of regulator shaft 32.

Regulators 10, 30 and 39 serve as blocking means to regulate the quantity of fluid in syringe barrel 3.

Regulator 10 comprises regulator section 11 and regulator section 12. Regulator section 11 has trough opening 17. Regulator section 12 has trough-type opening 18. Regulator sections 11 and 12 are secured together to comprise regulator 10. Regulator 10 fits around plunger 5. Plunger 5 sits in the trough-type openings 17 and 18, while regulator 10 snugly fits around plunger 5. Regulator 10 is thereby secured on plunger 5. Regulator 10 is designed to be of a specific length so that when the plunger end 7 is pressed toward barrel opening and stop 9, end 13 of regulator section 11 is pressed against barrel opening and stop 9, and end 16 of regulator section 12 is pressed against plunger end 7.

FIG. 2 is a top view of regulator 10. If a different dosage is desired, other than that determined by the length of regulator 10 when comprised of regulator sections 11 and 12, more regulator sections may be added. FIG. 2 shows a center regulator section 21. Center regulator section 21 has ends 22 and 23, and trough-type opening 52. Regulator section 11 has ends 13 and 14. Regulator section 12 has ends 15 and 16. End 14 of regulator section 11 has opening 19. End 15 of regulator section 12 has opening 20. End 22 of regulator section 21 has opening 24. End 23 of regulator section 21 has opening 25.

End 14 of regulator section 11 has inset 26. End 22 of regulator section 21 has insert 27. End 23 of regulator section 21 has insert 28. End 15 of regulator section 12 has insert 29.

Center regulator section 21 is secured to regulator sections 11 and 12 by inserting insert 27 into opening 19, insert 26 into opening 24, insert 28 into opening 20 and insert 29 into opening 25.

As shown in FIG. 2, other sections could be added to extend the length of regulator 10. These sections will be of specific lengths, with each specific length related to a difference in the distance which the plunger 5 will extend into syringe barrel 3 and thereby change the exact amount of dosage of the medication within syringe barrel 3 by a precise amount.

FIG. 3 is a top view of the regulator 39 which is shown in FIG. 1. In FIG. 1, regulator 39 comprises regulator section 40 and regulator section 41. Connected to regulator section 40 is barrel grip 37 with opening 38. Connected to regulator section 41 is plunger stop 42.

Barrel grip 37 fits around syringe barrel 3, with syringe barrel 3 fitting within opening 38. Regulator 39 is attached to syringe barrel 3 by bar grip 37 and extends beyond the plunger end 7 in a manner so that plunger end 7 can only be drawn out until it hits plunger stop 42. Regulator 39 therefore restricts the length to which the plunger end 7 may be pulled away from the barrel opening and stop 9.

In practical use, the barrel grip 37 will press against syringe stop 8 and the plunger 5 may be pulled out until plunger end 7 hits plunger stop 42. This will restrict the plunger head 6 in its movement away from the needle and thereby determine the dosage within the syringe barrel 3 at the time the syringe barrel 3 is being filled.

In FIG. 3, a center regulator section 46 is shown added to regulator 39. Regulator 39 may be extended in length by use of one or more additional sections, such as section 46, which enables the regulator 39 to be of differing lengths. This enables the distance which plunger end 7 may be extended, before it presses against plunger stop 42, to be extended and enables more medication to be placed within the syringe barrel 3.

The present invention would enable confident regulation of dosages of drugs to be administered by syringes away from physician's offices, clinics, hospitals, and similar institutions. Readjustment of the dosage level would be able to be accomplished by substitution of a new regulator or by changing the pre-set regulator dosage. The invention may also be used by permanently attaching a regulator in the pre-described manner to a syringe.

Any desired dosage may be pre-set by the use of additional regulator sections or changing the end regulator sections of regulators 10 and 39. Other changes and additions may be made to the present invention by use of springs, differing clasps, end pieces, etc.

While the invention has been described with reference to specific embodiments, the description is illustrative and is not to be construed as limiting the scope of the invention. Various modifications and changes may occur to those skilled in the art without departing from the spirit and scope of the invention as defined by the appended claims.

I claim:

1. A device for regulating the dosage of a fluid in a syringe having a plunger with a fluid-holding barrel and a stop at the top of said fluid-holding barrel comprising blocking means removeably secured to the plunger of the syringe placed between the plunger end of the syringe and the stop at the top of the syringe fluid-holding barrel, said blocking means comprising a top portion, a bottom portion, two side portions, two end portions, and an arcular trough type opening extending from one end portion to the other end portion through said top portion; said blocking means working automatically without being held manually;

whereby, during the filling of the filling of the syringe, when said plunger end is pressed toward said top, said blocking means allows any excess fluid to be rejected from said fluid-holding barrel, retaining only the desired dosage of said fluid in said barrel.

2. A device according to claim 1 wherein said blocking means comprises a regulator comprising:
 a. a plurality of sections secured together, and
 b. said arcular trough-type opening comprising a plurality of troughtype openings, one in each of said plurality of sections and forming a single arcular trough-type opening of length equal to the total length of said plurality of trough-type openings;
 whereby the plunger of said syringe may be placed within the single arcular trough-type opening with sufficient pressure on said plunger to secure said regulator to said plunger.

3. A device according to claim 2 wherein said plurality of sections comprises two end sections and a plurality of center sections whereby said plurality of center sections may be added to increase the length of said regulator and thereby change the desired dosage of said fluid in said barrel.

4. A device according to claim 3 wherein each of said two end sections comprises a blocking end which may press against either said plunger end of the syringe or said stop at the top of the syringe fluid-holding barrel; and a connecting end which is secured to another of said plurality of sections of said regulator.

5. A device according to claim 4 wherein each of said two end sections further comprises an insert extending from said connnecting end and an opening in said connecting end.

6. A device according to claim 5 wherein said two end sections of said regulator are secured together by placing the insert on the first end section into the opening on the second end section and the insert on the second end section into the opening on the first end section.

7. A device according to claim 6 wherein each of said plurality of center sections has two connecting ends for securing said plurality of center sections to said two end sections to form said regulator.

8. A device according to claim 7 wherein each of said two connecting ends has an insert extending from it and an opening extending into it.

9. A device for regulating the dosage of a fluid in a syringe having a plunger with a fluid-holding barrel and a stop at the top of said fluid-holding barrel comprising blocking means a plunger grip having two ends and an opening, operative to attach said regulator to the syringe plunger; and a shaft connected to said plunger grip, extending within the syringe fluid-holding barrel and pressing against the syringe plunger head, said blocking means being placed within the syringe fluid-holding barrel and pressing against the syringe plunger head whereby the syringe plunger head is restricted from movement past a pre-determined point thereby restricting the quantity of fluid which may be drawn into said fluid-holding barrel to a pre-determined dosage during the filling of the syringe.

10. A device according to claim 9 wherein said blocking means is also pressed against the stop at the top of the syringe fluid-holding barrel.

11. A device according to claim 10 wherein one end of said plunger grip is pressed against the stop at the top of the syringe fluid-holding barrel and the second end is pressed against by a force means to stabilize said regulator.

12. A device according to claim 11 wherein said syringe plunger fits snugly within said opening in said plunger grip in order to secure said regulator to said syringe plunger.

13. A device according to claim 12 wherein said shaft may be of varying lengths in order to change the predetermined point to which the syringe plunger head may be moved in order to change the pre-determined dosage.

14. A device for regulating the dosage of a fluid in a syringe having a plunger with a fluid-holding barrel and a stop at the top of said fluid-holding barrel comprising blocking means secured to the syringe barrel and operative to stop movement of the syringe plunger end; said blocking means being a regulator comprising:
 a. a plurality of sections secured together;
 b. a barrel grip connected to the end of one of said plurality of sections and securing said regulator to said syringe barrel; and
 c. a plunger stop connected to the end of another of said plurality of sections and operative to restrict movement of said syringe plunger;

whereby movement of the syringe, during the filling of the syringe plunger end is restricted, thereby restricting the quantity of fluid which may be drawn into the syringe barrel to a pre-determined dosage.

15. A device according to claim 14 wherein said plurality of sections comprises two end sections and a plurality of center sections whereby said plurality of center sections may be added to increase the length of said regulator and thereby change the desired dosage of said fluid in said syringe barrel.

16. A device according to claim 15 wherein one of said two end sections contains a barrel grip and a first connecting means and the other of said two end sections contains a plunger stop and a second connecting means.

17. A device according to claim 16 wherein said first and second connecting means are an insert in one end section and an opening in the other end section, whereby said insert may be placed in said opening to secure the end sections together.

18. A device according to claim 17 wherein each of said plurality of center sections has two ends with an insert extending from one end and an opening in the other end, whereby a desired number of said plurality of center sections may be secured between said two end sections to increase the length of said regulator and thereby change the desired dosage of said fluid in said syringe barrel.

* * * * *